(12) United States Patent
Ellis et al.

(10) Patent No.: US 7,831,293 B2
(45) Date of Patent: Nov. 9, 2010

(54) METHOD OF DEFINING A BIOLOGICAL TARGET FOR TREATMENT

(75) Inventors: Rodney Jay Ellis, Westlake, OH (US); Deborah A. Kaminsky, Big Bay, MI (US)

(73) Assignee: Advanced Clinical Solutions, Inc., Marquette, MI (US)

( * ) Notice: Subject to any disclaimer, the term of this patent is extended or adjusted under 35 U.S.C. 154(b) by 415 days.

(21) Appl. No.: 11/381,401

(22) Filed: May 3, 2006

(65) Prior Publication Data

US 2006/0258933 A1 Nov. 16, 2006

Related U.S. Application Data

(60) Provisional application No. 60/679,479, filed on May 10, 2005.

(51) Int. Cl.
A61B 5/05 (2006.01)
(52) U.S. Cl. .................. 600/424; 600/407; 600/414; 600/415; 600/426; 600/429; 606/130
(58) Field of Classification Search ............... 600/426, 600/410–420, 409, 439, 407; 606/23; 424/1.73
See application file for complete search history.

(56) References Cited

U.S. PATENT DOCUMENTS

| | | | | |
|---|---|---|---|---|
| 4,460,559 | A | | 7/1984 | Goldenberg |
| 5,682,890 | A | * | 11/1997 | Kormos et al. ............... 600/417 |
| 5,891,034 | A | * | 4/1999 | Bucholz ..................... 600/426 |
| 6,056,700 | A | | 5/2000 | Burney et al. |
| 6,173,175 | B1 | | 1/2001 | Alazma et al. |
| 6,173,201 | B1 | * | 1/2001 | Front .......................... 600/429 |
| 6,347,240 | B1 | * | 2/2002 | Foley et al. ................. 600/426 |
| 6,350,244 | B1 | | 2/2002 | Fisher |
| 6,368,331 | B1 | * | 4/2002 | Front et al. ................. 606/130 |
| 6,560,354 | B1 | * | 5/2003 | Maurer, Jr. et al. .......... 382/131 |
| 6,567,687 | B2 | * | 5/2003 | Front et al. ................. 600/426 |
| 6,725,080 | B2 | * | 4/2004 | Melkent et al. ............. 600/424 |
| 6,824,516 | B2 | | 11/2004 | Batten et al. |
| 6,826,422 | B1 | * | 11/2004 | Modell et al. .............. 600/407 |
| 7,001,341 | B2 | * | 2/2006 | Gellman et al. ............. 600/562 |
| 7,162,292 | B2 | * | 1/2007 | Ohno et al. ................. 600/407 |
| 7,379,769 | B2 | * | 5/2008 | Piron et al. ................. 600/415 |
| 2002/0026127 | A1 | * | 2/2002 | Balbierz et al. ............. 600/567 |
| 2002/0107437 | A1 | | 8/2002 | Sirimanne et al. |
| 2002/0146371 | A1 | * | 10/2002 | Li et al. ....................... 424/1.73 |
| 2004/0106869 | A1 | * | 6/2004 | Tepper ........................ 600/443 |
| 2004/0133101 | A1 | * | 7/2004 | Mate et al. .................. 600/426 |
| 2005/0035296 | A1 | * | 2/2005 | Kojima et al. ............. 250/363.03 |
| 2005/0038355 | A1 | * | 2/2005 | Gellman et al. ............. 600/564 |
| 2005/0053607 | A1 | * | 3/2005 | Bates et al. ................. 424/155.1 |
| 2005/0080333 | A1 | | 4/2005 | Piron et al. |
| 2005/0159676 | A1 | | 7/2005 | Taylor et al. |
| 2006/0258933 | A1 | * | 11/2006 | Ellis et al. ................... 600/407 |
| 2007/0016014 | A1 | * | 1/2007 | Hara et al. .................. 600/426 |
| 2008/0221439 | A1 | * | 9/2008 | Iddan et al. ................. 600/424 |
| 2008/0221440 | A1 | * | 9/2008 | Iddan et al. ................. 600/424 |

FOREIGN PATENT DOCUMENTS

EP 1506742 A * 2/2005

OTHER PUBLICATIONS

John E. Sylvester, M.D., et al., "Ten-year biochemical relapse-free survival after external beam radiation and brachytherapy for localized prostate cancer: the Seattle experience", Int. J. Radiation Oncology Biol. Phys., vol. 57, No. 4, pp. 944-952, 2003.

Winston E. Barzell, M.D., et al., "How to perform transperineal saturation prostate biopsy", Urology Times, http://ut.adv100.com/urologytimes/contect/printContentPopup.jsp?id+56612, printed Feb. 11, 2004.

George L. Wright, Jr., PhD., et al., "Expression of prostate-specific membrane antigen in normal, benign, and malignant prostate tissues", Urol Oncol 1995; 1:18-28.

Rodney J. Ellis, M.D., et al., "Radioimmunoguided imaging of prostate cancer foci with histopathological correlation", Int. J. Radiation Oncology Biol. Phys., vol. 49, No. 5, pp. 1281-1286, 2001.

Rodney J. Ellis, M.D., et al., "Four-year biochemical outcome after radioimmunoguided transperineal brachytherapy for patients with prostate adenocarcinoma", Int. J. Radiation Oncology Biol. Phys., vol. 57, No. 2, pp. 362-370, 2003.

Gordon L. Grado, M.D., et al., "Actuarial disease-free survival after prostate cancer brachytherapy using interactive techniques with biplane ultrasound and fluoroscopic guidance", Int. J. Radiation Oncology Biol. Phys., vol. 42, No. 2, pp. 289-298, 1998.

Michael J. Zelefsky, M.D., et al., "Dose escalation with three-dimensional conformal radiation therapy affects the outcome in prostate cancer", Int. J. Radiation Oncology Biol. Phys., vol. 41, No. 3, pp. 491-500, 1998.

D. Bruce Sodee, et al., "Prostate cancer and prostate bed SPECT imaging with ProstaScint®: semiquantitative correlation with prostatic biopsy results", The Prostate 37:140-148, 1998.

(Continued)

*Primary Examiner*—Brian Casler
*Assistant Examiner*—Baisakhi Roy
(74) *Attorney, Agent, or Firm*—Pearne & Gordon LLP

(57) ABSTRACT

A method of defining a biological target for treatment in which image detectable markers are placed at and correlated to the location or locations of tissue biopsy. By obtaining pathological analysis of the biopsy tissue specimens and correlating the analysis to the corresponding marker locations, the definitive pathological analysis of the target tissue at the marker locations can be correlated to corresponding locations on a functional image of the target tissue. The correlation of the marker locations and pathology to the corresponding locations on a functional image can then be used to prescribe and apply modulated therapy to the target tissue.

31 Claims, No Drawings

OTHER PUBLICATIONS

Jean M. Moran, et al., "Radiotherapy: what can be achieved by technical improvements in dose delivery?", Lancet Oncol 2005; vol. 6, pp. 51-58, Jan. 2005.

Mehraj Sheikh,M.D., et al., "Patients' tolerance and early complications of transrectal sonographically guided prostate biopsy: prospective study of 300 patients", Journal of Clinical Ultrasound, vol. 33, No. 9, pp. 452-456, Dec. 2005.

Yan Yu, et al., "Permanent prostate seed implant brachytherapy: report of the American Association of Physicists in Medicine Task Group No. 64[a)]", Med. Phys. 26(10), pp. 2054-2076, Oct. 1999.

Juanita M. Crook, et al., "Critical organ dosimetry in permanent seed prostate brachtherapy: defining the organs at risk", Brachytherapy 4 (2005), pp. 186-194.

Chiaho Hua, Ph.D., et al., "Development of a semi-automatic alignment tool for accelerated localization of the prostate", Int. J. Radiation Oncology Biol. Phys., vol. 55, No. 3, pp. 811-824, 2003.

Zhenghong Lee, et al., "Multimodal and three-dimensional imaging of prostate cancer", Computerized Medical Imaging and Graphics 29 (2005), pp. 477-486.

Emile N.J.T. van Lin, M.D., et al., "IMRT boost dose planning on dominant intraprostatic lesions: gold marker-based three-dimensional fusion of CT with dynamic contrast-enhanced and $^1$H-spectroscopic MRI", Int. J. Radiation Oncology Biol. Phys., vol. 65, No. 1, pp. 291-303, 2006.

Gregory S. Merrick, M.D., et al., "Erectile function after prostate brachytherapy", Int. J. Radiation Oncology Biol. Phys., vol. 62, No. 2, pp. 437-447, 2005.

Daphna Y. Gelblum, M.D., et al., "Rectal complications associated with transperineal interstitial brachtherapy for prostate cancer", Int. J. Radiation Oncology Biol. Phys., vol. 48, No. 119-124, 2000.

Kenneth Hu, M.D., et al., "Clinical course of rectal bleeding following I-125 prostate brachytherapy", Int. J. Radiation Oncology Biol. Phys., vol. 41, No. 2, pp. 263-265, 1998.

Jean Pouliot, Ph.D., et al., "(Non)-Migration of radiopaque markers used for on-line localization of the prostate with an electronic portal imaging device", Int. J. Radiation Oncology Biol. Phys., vol. 56, No. 3, pp. 862-866, 2003.

Peter D. Grimm, et al., "Technical improvement in permanent seed implantation: a two-stage brachytherapy system. Description and comparison with current technique", Brachtherapy 3 (2004), pp. 34-40.

Rodney, J. Ellis, et al., "Translation of SPECT/CT Guided Prostate Brachytherapy to a community setting from the university setting with a case example of histopathologic correlation to the image set", Society of Nuclear Medicine 52nd Annual Meeting Poster 1423; J Nucl Med Suppl 2005; 24(2):439 (abstract).

Eclipse™ Integrated Treatment Planning, Brachytherapy, Varian Medical Systems, Oncology Systems, RAD 7154, Oct. 2002 (300).

Eclipse™ Integrated Treatment Planning, Plan Evaluation, Varian Medical Systems, Oncology Systems, RAD 7159, Oct. 2003 (6M).

Robert C. Susil, et al., "System for prostate brachytherapy and biopsy in a standard 1.5 T MRI scanner", Magnetic Resonance in Medicine, vol. 52, Issue 3, pp. 683-687, published online Aug. 23, 2004 (abstract).

Frauscher, F., et al., "Comparison of contract enhanced color Doppler targeted biopsy with conventional systematic biopsy: impact of prostate cancer detection", J. Urol. Apr. 2002; 167(4): 1648-52 (abstract).

Leonard R. Coover, et al, "Breast tumor localization using sestamibi. ", Clinical Nuclear Medicine, Vo. 27, No. 3, pp. 161-164.

Welsh JS, et al., "Fiducial markers implanted during prostate brachytherapy for guiding conformal external beam radiation therapy", Technol. Cancer Re. Treat. 2004; 3:359-64 (abstract).

Deborah Rhodes, et al., "Molecular breast imaging: a new technique using technetium Tc 99m scintimammography to detect small tumors of the breast", May Clinic Proceedings, Jan. 2005, vol. 80, Issue 1, pp. 24-30 (abstract).

Leonard R. Coover, MD, et al., "Scintimammography with dedicated breast camera detects and localized occult carcinoma", The Journal of Nuclear Medicine, Vo. 45, No. 4, Apr. 2004, pp. 553-558.

Letters to the Editor, The Journal of Nuclear Medicine, vol. 46, No. 3, Mar. 2005, pp. 550-551.

Brian M. Kruger, et al., "Accuracy of marker clip placement after Mammotome breast biopsy", CARJ vol. 53, No. 3, Jun. 2002, pp. 137-140.

Ancona A., et al., "Digital stereotactic breast microbiopsy with the mammotone: study of 122 cases", Radiol Med (Torino), May 2001; 101(5):341-7 (abstract).

Ariche-Maman S., et al., "Value of ultrasound detection of post-Mammotome scar for preoperative localization of breast microcalcifications", J. Radiol. 2003 No. 84(11 Pt 1):1747-51 (abstract).

Kubota K., et al., "Magnetic resonance imaging of the metal clip in a breast: safety and its availability as a negative marker", Breast Cancer, 2004: 11(1):55-9 (abstract).

Margolin FR., et al., "Metallic marker placement after stereotactive core biopsy of breast calcifications: comparison of two clips and deployment techniques", AJR Am J Roentgenol. Dec. 2003; 181(6):1685-90 (abstract).

Rosen EL, et al., "Accuracy of a collagen-plug biopsy site marking device deployed after stereotactic core needle breast biopsy", AJR Am J Roentgenol. Nov. 2003 191 (5):1295-9 (abstract).

Schulz-Wendtland R., et al., "Do tissue marker clips after sonographically or stereographically guided breast biopsy improve follow-up of small breast lesions and localisation of breast cancer after chemotherapy?", Rofo May 2002; 174(5):620-4 (abstract).

F. Burbank, et al., "Tissue marking clip for stereotactic breast biopsy: initial placement accuracy, long-term stability, and usefulness as a guide for wire localization", Radiology, Nov. 1997: 205(2):407-15 (abstract).

R.P. Goldberg, et al., "Preoperative localization of nonpalpable breast lesions using a wire marker and perforated mammographic grid", Radiology, Mar. 1983; 146(3):833-5 (abstract).

F.M. Hall, et al., "Preoperative localization of nonpalpable breast lesions", AJR Am J Roentgenol. Jan. 1979; 132(1):101-5 (abstract).

E.S. Burnside, et al., "Movement of a biopsy-site marker clip after completion of stereotactic directional vacuum-assisted breast biopsy: case report", Radiology, 2001 No. 221(2): 504-7 (abstract).

S.G. Lee, et al., "Displacement of microcalcifications during stereotactic 11-gauge directional vacuum-assisted biopsy with marking clip placement: case report", Radiology, May 2001; 219(2):495-7 (abstract).

Amendment Under Article 34 and Response to Written Opinion submitted in International Application No. PCT/US2006/017185, Applicant: Advanced Clinical Solutions, Inc., dated Oct. 15, 2007.

International Search Report (PCT/US2006/17185) dated Aug. 15, 2007.

* cited by examiner

METHOD OF DEFINING A BIOLOGICAL TARGET FOR TREATMENT

BACKGROUND OF THE INVENTION

Early stage prostate cancer diagnosis and staging challenges patients and clinicians, as it has proven difficult to reliably distinguish indolent and incidental disease from progressive, life-threatening disease. Standard treatment for prostate cancer generally has been directed at the entire organ or perhaps specific organ regions found generally to have a higher incidence of tumor burden, rather than at point source identification of pathologically confirmed regions of tumor. Traditionally, organ-targeted prostate cancer treatments have been accomplished either by surgical resection of the gland, or by directing multiple beams of radiation into the pelvis to encompass the entire gland in a uniform dose. In the case of prostate cancer, tumor is not partially resected surgically for treatment, as is the case in breast and other cancers. Rather, the entire prostate gland is removed during surgical intervention. Radiation treatments for prostate cancer also treat the gland and glandular areas found to have higher incidence of tumor burden, often having the impact of over-exposing normal radiosensitive tissues to unnecessary treatment, thereby increasing the likelihood of treatment related morbidities. Such poorly directed curative therapies lead to increased cost of care and decreased patient quality of life.

Alternate methods such as cryotherapy have also been explored, though again generally directed to treat, or freeze, the entire organ. While newer focal cryotherapy methods attempt to more uniquely focus the freezing process to a section of the gland in order to decrease the incidence of treatment related morbidity, appropriate targeting methods continue to rely on general assumptions about the location of areas of high tumor burden.

As computers have become better at assisting in treatment planning, it has become standard to use three dimensional (3-D) treatment planning to shape the individual field for radiation therapy to treat, for example, only the prostate itself, commonly utilizing a minimal margin of about 5 to 15 millimeters beyond the edges of the gland. Use of this planning convention allows for higher doses of radiation to be delivered while at the same time sparing the surrounding tissue and limiting morbidity. Clinical trials have confirmed that by using higher doses of radiation in a 3-D conformal approach, higher cure rates are achieved with lower toxicity.

An alternative method for achieving a high dose delivered to the entire gland is known as brachytherapy, or the placement of either temporary High Dose Rate (HDR) or permanent Low Dose Rate (LDR) radioactive sources within the prostate. These therapies allow focal radiation therapy targeting to within 10 millimeters of the glandular areas generally identified as at high risk of containing tumor. Target treatment margins for brachytherapy are typically adopted in the range of 1-10 mm. A gross target volume (GTV) of a treatment target may be defined by anatomic image studies, which may then be used to further define a clinical target volume (CTV), typically comprising the GTV plus an adequate margin to account for microscopic disease at the edge of the GTV and allowance for motion of the GTV from patient positioning variation during image study. Rarely are permanent or temporary sources placed more than 10 mm beyond either the CTV or GTV. For brachytherapy (LDR and HDR), the CTV often is equal to the GTV as there is no motion of the organ that does not include the sources, and daily set-up errors can be eliminated. A biological target volume (BTV) typically represents a region defined by a functional study that may be completely within the GTV, or may expand the GTV by showing disease extending beyond the margins defined by the GTV on the anatomic study.

More recently, again enabled in large part through improved computer software, a newer external beam radiation therapy technique, referred to as Intensity Modulated Radiation Therapy or IMRT, has become available for treating the entire organ with tighter margins of as little as 4 millimeters. IMRT provides options for targeting small volume (<1 cc) regions within a treatment planning volume (TPV) to focus higher doses than the dose delivered to the entire gland volume, comprised of the CTV, GTV and BTV. This focused IMRT treatment method, as described, is currently utilized in only a minority of select academic settings using functional images acquired with either Magnetic Resonance Spectroscopy Imaging (MRSI) or Single Photon Emission Computerized Tomography (SPECT) images to help define a region within the prostate gland believed to represent occult tumor volumes. These identified areas found to be suspicious for occult tumor on functional imaging represent findings which are indistinguishable with standard anatomic studies such as Computerized Axial Tomography (CAT or CT) scan, Magnetic Resonance Imaging (MRI) used in conjunction with Ultrasound (US) and/or US alone. While the SPECT imaging techniques rely on over expression of a specific protein identified by a radiolabeled monoclonal antibody, the MRSI technique utilizes voxel analysis of tissue composition to detect regions felt more likely to represent cancerous regions. Newer functional studies will certainly be developed in the future using similar technologies, such as Positron Emission Tomography (PET) tracers, Optical Biopsy techniques, or other similar technologies.

As discussed in more detail below, the method of the invention will enable the more effective utilization of the foregoing image modalities to localize and treat cancer within a particular target organ with tumor site localization confirmation to histopathological findings in order to more effectively target dose escalation to BTV while sparing surrounding tissues from unnecessary treatment.

Because standard image techniques (CAT, MRI, X-ray, US) are unable, in routine clinical use, to visualize specific regions containing tumor within the gland, it remains a significant problem for current therapies, resulting in increased treatment related morbidity and overall cost of care. In routine clinical practice, at the time a male patient presents with either a palpable abnormality on Digital Rectal Exam (DRE) or, more commonly, with an elevated Prostate Specific Antigen (PSA) level on a blood test, a biopsy of the gland is recommended by the physician to determine if a cancer is present. The patient's initial biopsy procedure is typically performed in the office of a urologist. Frequently, this first procedure is completed with the patient in lateral decubitus position utilizing a Trans-Rectal Ultrasound (TRUS) probe that allows biopsy sample to be taken through the TRUS probe. Sextant biopsy is regarded as the standard of reference for nonsurgical tumor localization, although limitations of sextant biopsy are increasingly recognized.

During a standard sextant biopsy procedure, typically six to twelve biopsy tissue samples will be obtained from the prostate gland with each biopsy sample involving an individual needle pass through the rectal wall and into the desired location within the gland for the biopsy. Standard sextant biopsies are directed into both the right and left general regions of the prostate gland, and may further be directed into the right and left base, mid and/or apex regions of the gland at either medial or lateral locations. Recently, it has become more common to have biopsy tissue samples recorded as to the rudimentary region within the gland from which it was obtained (medial/lateral-right/left: base, mid or apex). In addition, pathologists are more frequently in standard practice being requested to record and report the percentage of each biopsy core involved with tumor to help determine if the region of biopsy has minimal disease or bulky tumor deposits.

When a patient presents as highly suspicious for disease (e.g., rising PSA or positive DRE) and disease confirmation cannot be validated by a positive biopsy result, patients more commonly today undergo saturation biopsy procedures whereby 24-36 biopsy tissue samples are taken, making it increasingly difficult and costly to record and track the region within the gland from which the sample was obtained. Most often, only positive biopsy samples are reported for rudimentary location. Most importantly, the precise location of each biopsy sample cannot be determined even with the use of imaging studies following the biopsy procedure because the sextant localization of disease is not synonymous with volumetric localization of tumor. As such, there is no effective means of correlating the specific pathology of the biopsy site to its location in the target organ or tissue in a manner that will effectively facilitate precise localization of positive histopathology to identify tumor volumetric localization for use in treatment planning targeting. Cancer patients, such as prostate, are frequently followed for extended time periods between diagnosis, medical imaging, treatment and post-therapy follow-up. These patients are, therefore, evaluated over time by different physicians (e.g., urologists and radiation oncologists) in a number of settings (e.g., physician office, outpatient hospital imaging, surgical center) and with various imaging and image-guided treatment modalities requiring different patient positioning during imaging (supine) and treatment (lateral decubital) which, collectively, serve to obscure correlation of pathology information with in-vivo image sets.

Thus, there remains a need for the ability to refine the identification and volumetric location of disease as correlated to positive histopathology within the suspect organ or tissue, and to be able to use these refined data sets to direct therapy in a more effective and less harmful manner. It has been estimated that each year in the U.S. over one million biopsies are performed, with as many as 50% of those core samples being reported as negative. In the example of standard core biopsy sampling techniques for the prostate gland collecting 6 to 12 standard core samples per patient, millions of core tissue biopsy samples are evaluated each year. The clinical inefficiency of the biopsy procedure results in a large negative burden to patients for non-productive procedures correlating to increased risk for procedure related morbidities (e.g., fever, infection and bleeding, discomfort, and lost productivity), for the often ineffective procedure. In addition, the pathology results are routinely lost to discreet anatomic localization for use in therapy planning.

SUMMARY OF THE INVENTION

As noted, a key issue for local cancer therapies such as radiation oncology is the term 'dose response' stating that cancers such as prostate cancer have a higher cure rate for a higher delivered dose. With Intensity Modulated Radiation Therapy (IMRT) or other local therapies such as cryotherapy, focal cryotherapy, thermotherapy, chemoembolization and photodynamic therapy, physicians can 'paint' a high dose of the local therapy to relatively small volumes; although lacking is an ability to accurately identify discrete areas of tumor, such that unintended treatment to normal treatment sensitive tissues can be minimized in order to decrease damage to surrounding tissues such as the rectum or bladder.

In accordance with the method of the invention, the placement of detectable markers at the site of biopsy will allow treatment planning to take into consideration the points within a target area or volume that are histopthologically confirmed to have tumor, how much of each core sample was replaced by tumor, as well as other factors warranting dose modulation such as genetics, proteomics, percent tumor burden, Gleason score, tumor marker positive, PSA, prostatic intraepithelial neoplasia (PIN) status, metastatic phenotypes, gene expression signature and so on. In this way, higher doses can be prescribed to these points or discrete volumes as defined by positive biopsy results and, if the marker did not verify cancer at its position; that region may be spared a higher dose or possibly even receive a decreased dose. Significantly, the pathologically defined points for tumor may be correlated to a functional study (e.g., MRSI, SPECT, PET or Optical Biopsy), such that positive findings on the functional image can serve as an internal marker for known disease sites. If the functional study is able to detect these areas of heretofore occult tumor foci, then other areas showing activity on the functional study can be treated as representing additional occult tumor foci; and thereby used to define a biological target volume for treatment.

Thus, in accordance with the present invention there is provided a method of correlating a functional image of a target tissue to the definitive pathology of the target tissue comprising obtaining at least one biopsy specimen from the target tissue at a corresponding biopsy location, placing a detectable marker substantially at the biopsy location, and correlating said marker to said biopsy location, such as by recording, manually or otherwise, the identity or type of marker to the location from the target tissue from which it was excised. A pathological analysis of the biopsy specimen is obtained and likewise correlated to the biopsy, and marker, location in the target tissue. By obtaining at least one anatomic image of the target tissue which detects the location of at least one said detectable marker, and obtaining at least one functional image of said target tissue, the location of the detectable markers can be correlated with corresponding locations on the functional image, whereby the pathological analysis of the target tissue corresponding to the location of the detectable markers can be correlated to a diagnosis of the target tissue produced by the functional image at the location or locations of the detectable markers.

Upon correlation of the aforementioned image data, further aspects of the method of the invention comprise prescribing therapy to the target tissue based on said correlation or, depending upon the diagnosis, prescribing one or more additional biopsies to the target tissue at locations other than the locations of the detectable markers. In some aspects of the invention, where the functional imaging is indicative, the method of the invention will comprise applying therapy to the target tissue in at least one region shown by the functional image to be suspicious for cancer. In other applications the inventive method comprises correlating the location of at least one said detectable marker whose corresponding pathological analysis is positive for cancer, with a location of said target tissue shown by at least one functional image to be suspicious for cancer, and prescribing and/or applying therapy to the target tissue in at least one other region shown by said functional image to be suspicious for cancer. In various embodiments, the applied therapy is selected from IMRT, EBRT, Cryotherapy, LDR, HDR, Hyperthermia, Brachytherapy, Photo Dynamic Therapy, High Intensity Focused Ultrasound (HIFU), and Gene Therapy. As will be apparent from the instant disclosure, the method of the invention is particularly useful when the target tissue is a prostate, though the method of the invention is not so limited in its application.

In certain aspects of the invention, the said anatomic imaging is selected from CT, MR, X-ray, US, Fluoroscopy or a combination or hybrid thereof, and the said functional imaging is selected from SPECT, PET, MRSI, Optical Biopsy or a combination or hybrid thereof. In one aspect of the method of the invention, the anatomic and functional images are acquired substantially simultaneously. More preferably, the said images are acquired as a hybrid or combination image and, more preferably still, the said hybrid or combination image is selected from SPECT/CT, PET/CT, SPECT/MR, PET R, MRSI, SPECT/MR/CT, SPECT/MR/US, SPECT/CT/US, SPECT/CT/MRSI/US, SPECT/X-ray, CT/SPECT/X-ray, PET/X-ray and CT/PET/X-ray. In another aspect of the method of the invention, the anatomic and functional images are acquired separately. In preferred embodiments, the separately acquired images will be co-registered or fused using image fusion software.

As will be apparent, the method of the invention frequently comprises obtaining biopsy specimens and placing detectable markers substantially at multiple biopsy locations. In these embodiments, a plurality of said markers are ideally distinguishable from each other by at least one said anatomic image, functional image or a combination or hybrid thereof, such as by their size, shape, image intensity, acoustical impedance, digital signal from a chip, etc. or wavelength. Said markers may also be used to simultaneously track, record and/or report therapeutic dosimetry delivery over time and/or patient position.

In carrying out these embodiments, the method comprises obtaining a plurality of biopsy specimens from said target tissue at a corresponding plurality of biopsy locations; placing a detectable marker substantially at each said biopsy location, and correlating each said marker to each said biopsy location. A pathological analysis of each said biopsy specimen is then obtained and correlated to each said biopsy location. Upon obtaining at least one anatomic image of said target tissue which detects the location of one or a plurality of said detectable markers and obtaining at least one functional image of said target tissue, the locations and corresponding pathological analyses of said plurality of detectable markers is correlated with corresponding locations on said at least one functional image. Thus, in accordance with the inventive method, one or more biological target volumes is defined based on said marker locations, pathological analyses and evidence of uptake and/or a diagnosis produced by said at least one functional image at each said marker location; and, therapy is prescribed and/or applied to one or more said biological target volumes; and/or, one or more additional biopsies is prescribed and/or obtained from said target tissue at locations other than said marker locations.

In carrying out the invention, where indicated, therapy is applied to at least a portion of at least one said biological target volume at a different intensity than an intensity applied to at least one other portion of said target tissue. In some embodiments, the process of applying therapy comprises inputting a treatment intensity to be applied to at least one said biological target volume into an electronic treatment planning system As noted, the applied therapy is preferably selected from IMRT, EBRT, Cryotherapy, LDR, HDR, Hyperthermia, Brachytherapy (LDR and HDR), Photo Dynamic Therapy, HIFU and/or Gene Therapy.

These and other embodiments, and a fuller understanding of the invention will be had from the following detailed description of the preferred embodiments.

DETAILED DESCRIPTION OF THE INVENTION

The method of the invention provides an advantageous means of defining a biological target area in a target tissue such as the prostate which then can be used to indicate and guide subsequent treatment, as well as to guide future biopsies. In particular, by placing an image detectable marker at the site of each biopsy at the time of the biopsy procedure, the marker can then be visualized and tracked after the procedure to provide specific correlation to point locations of either benign or cancerous tissue. The ability to visually locate the point site of each biopsy can then be useful not only to assist in planning and modulating therapy for patients with positive biopsy, but also for subsequent image guided biopsy for those patients whose PSA remains elevated or rises further following the initial biopsy when the initial tissue samples fail to provide confirmation of malignancy, and a subsequent biopsy is recommended. For use in repeat biopsy, the urologist can utilize previously placed biopsy markers to visualize the locations of the previous negative biopsies and acquire additional samples from new locations, optionally leaving visually distinguishable markers in the new locations for subsequent biopsy or treatment localization, as needed. Once a diagnosis of cancer has been established through positive biopsy determination, these same markers can then be used to help direct therapy for the patient. Ideally, therapy can be delivered by, for example, External Beam Radiation Therapy (EBRT), Intensity Modulated Radiation Therapy (IMRT), Brachytherapy (HDR and LDR) or cryotherapy, using the known point of cancer for dose intensification or escalation, thereby increasing therapy dose to the tumor while simultaneously sparing excessive therapy to regions believed to be unlikely to contain disease.

Key to the advantages of the inventive method is the placement of a suitable marker at a biopsy site and the correlation of the marker with the pathology of the corresponding biopsy specimen. The information and data subsequently gathered from the correlation of specific markers with specific biopsy specimens enables physicians to fine tune their diagnoses so as to accurately localize those regions of the target tissue which indicate cancer and to modify the application of therapy so as to maximize treatment intensity at those target areas where cancer is most progressed or aggressive, and to minimize treatment intensity in those target areas which indicate the absence of tumor or less tumor burden. This correlation of data becomes most important when imaging, diagnoses and treatment are obtained or performed by different physicians, at different facilities and at different times; which is typically the case.

In accordance with the invention, the biopsy or biopsies of the target tissue can be obtained by any means known to those of ordinary skill in the art. In the typical case, the biopsy will be image guided, such as by TRUS, CT or the like. Moreover, functional images acquired using scanners such as MRSI and SPECT or PET can be obtained simultaneously or co-registered with fusion software to produce hybrid SPECT/CT or PET/CT fused image data sets to guide the biopsy. Techniques suitable for use in accordance with the method of the invention will be apparent to those of ordinary skill in the art in view of the present disclosure and include, for example, transrectal or transperineal templates used with imaging to enable prostate biopsy needle placement to investigate carcinoma core distribution; TRUS sextant biopsies of the prostate; six or eight sector biopsies taken with a Manan biopsy gun using 18 gauge biopsy needles; saturation TRUS biopsy; multi-core biopsy; Augmented Reality (AR) guided biopsy; stereotactic vacuum-assisted biopsy; CT or MR guided biopsy; 3-D saturation biopsy mapping, radioimmunoscintographic hybrid image guided biopsy and so on. Suitable devices for carrying out these procedures, such as end-cut and standard side-notch instruments, fine needle aspiration sets, and breast lesion localization needles, are known in the art and commercially available from, for example, Core Biopsy Product Group (Aria reusable devices), Single Action Biopsy Devices (SABD disposable devices), Biopty, Magnum and BIP high speed multi-biopsy instruments (Bard), Ultra-Core biopsy needles and Tru-Core coaxial biopsy needle sets (MDTECH Medical Device Technologies, Inc.), Pro-Mag biopsy system (Manan Medical Products, Inc.), Centrica Rotational Core Biopsy/Rotational Core Biopsy Systems (Sanarus Cassi, Inc.) and TargetScan Biopsy Kit (Envisioneering, LLC), to name a few.

In carrying out the invention, an image detectable marker is placed at substantially the site of one or more of the biopsy sites where tissue was extracted for histological evaluation. Preferably markers are placed at multiple biopsy sites and, more preferably, at each biopsy site. Still more preferably, the markers are uniquely identifiable on imaging. As used herein, a marker is placed substantially at the site of biopsy if it is placed within about 15 mm, and more preferably within about 10 mm from where the biopsy specimen is excised. Ideally, the marker is placed directly at or adjacent the site. The detectable markers can be placed at the site of biopsy by any suitable means as would be apparent to those of ordinary skill in the art in view of this disclosure.

In preferred embodiments, the marker will be placed at the site of biopsy substantially simultaneously with the excision of the tissue from the biopsy site. Ideally, the markers can be placed at the biopsy site substantially simultaneously by a single instrument which will excise the tissue and leave a marker substantially in its place. As will be apparent to those of ordinary skill in the art in view of this disclosure, such a device can be configured any number of ways. Suitable such devices are described, for example, in U.S. Pat. Nos. 6,350,244 and 6,056,700, as well as Published Application Nos. 2005/0080333, 2005/0038355 and 2005/0080377, incorporated herein by reference. These and other means of placing the markers according to the invention at the site of biopsy will be apparent to those of ordinary skill in the art in view of the present disclosure.

The detectable markers can be any suitable material that will function to produce an image, representative graph or signal for co-registration to the particular image modalities used so that the biological target areas or volumes which correlate to positive findings on the biopsy pathology report can be subsequently used to define the BTV. Such markers can be in the form of clips, seeds, implants and the like, all as would be apparent to those of ordinary skill in the art in view of this disclosure.

As noted, suitable materials for said markers will depend upon the particular imaging modalities to be employed and the degree to which the markers must be distinguishable from one another by such modalities. Thus, desirable marker characteristics or combinations thereof will be, depending upon the image modalities, image intensity, such as it degree of radiopacity, fluorescence or echogenicity, image wavelength, size, shape and so on. Suitable marker materials will include gold, titanium, tantalum, rhodium, platinum, silver, iodine, collagen-plug, stainless steel, coated lead, combinations thereof and the like.

In some embodiments it may be desirable for the markers to be biodegradable. Such markers can be made from biodegradable and bioresorbable polymers, such as polymers and copolymers of alpha-hydroxy acids. Suitable polymers, such as polymers and copolymers of lactic acid, glycolic acid, lactide and glycolide can be prepared from or imbibed with materials having suitable radiopacity or other detectable qualities which, after providing their desired image, will degrade and be eliminated from the tissue over time. Thus, one can, for example, use a marker with a polylactic acid or other bioabsorbable material filled with iodine or other radiopaque material so that they are visible under X-ray or ultrasound. The radiopaque material may itself by bioabsorbable. Other suitable marker materials will be apparent to those of ordinary skill in the art in view of the instant disclosure.

In preferred embodiments, to facilitate tracking and recording, it is advantageous if the markers are visually distinguishable on the images. This is particularly desirable when subsequent biopsies are taken in the same general region of the target tissue. In this way, one can readily distinguish between, for example, right apex biopsy 1 and right apex biopsy 2. Thus, it will be apparent to those of ordinary skill in the art that the markers can be designed to provide visually distinguishable images each from the other, such as by shape, image intensity, wavelength or the like. For example, Visicoil markers, commercially available from IBA, Louvain la-Neuve, Belgium, are available in various lengths, which can be recorded into the data set for future reference. Similarly, Gentra Source, from Kawasumi Laboratories America, Inc., provides fine-wire coiled Rhodium structure which provides a unique image on CT. Still further, Best Gold 198 Seed inactive and fiduciary marker kits from Best Medical International, Inc., provide gold markers of varying dimensions (0.8 mm diameter in 3, 5 and 7 mm lengths; 1.0 mm diameter in 3, 5, 7 and 10 mm lengths; and, 1.2 mm diameter in 3 mm lengths), which can provide unique MRI and CT signals depending upon the marker diameter and length.

Similarly, non-radioactive so-called "cold seeds" may be commercially available which will produce unique image patterns. Various seed companies, such as Draximage, Mentor, North American Scientific and International Brachytherapy produce seeds which have unique design characteristics which are visually distinguishable on Xray or Fluoroscopy. Likewise, while most seeds are not visually distinguishable on CT or MRI, seeds with a high volume gold content may be detectable on MRI. Other suitable markers which may be visually distinguishable on various imaging modalities include a non-radioactive or "cold" TheraSeed Pd-103 from Theragenics, which will provide unique identification on X-ray or Fluoroscopy and a cold Iodine-125 Cold Echo Seed, from Amersham-GE Medical, which will provide unique identification on X-ray, Fluoroscopy and ultrasound. Biopsy site markers may be selected to include other functions, such as implanted electromagnetic transponders (Calypso® 4D Localization System, Calypso Medical) that track patient motion during fractionated dose treatments and metal oxide semiconductor field-effect transistor technologies (OneDose Patient Dosimetry System, Sicel Technologies) designed for in vivo measurement of patient dose during radiotherapy; when combined with the instant invention further augment dose delivery accuracy.

Tissue samples obtained at biopsy undergo pathology lab analysis to identify histopathologic evidence of tumor. A finding of positive (+) biopsy represents the definitive diagnosis of presence of disease. Thus, one can generate a data set comprising a series of marker locations, e.g., right apex, left apex and base, with their respective pathologies, e.g., benign, cancerous, benign. In accordance with the preferred embodiments, the pathology reports will not merely provide evidence of the presence or absence of disease, they will evaluate the tumors for aggressiveness of disease and include other pathological data which can be included in the data set correlated to the marker sites. Additional pathology data which can be included in the data set correlated to the marker site can include genetics, genetic markers, genomics, proteomics, percent tumor burden, Gleason score, tumor marker positive, PSA, percent fee PSA (PSA II), other cancer antigens, prostatic acid phosphatase (PAP), free testosterone, total testosterone, optical biopsy, prostatic intraepithelial neoplasia (PIN) status, metastatic phenotypes, gene expression signature and the like.

In order to derive the most significant advantages of the method of the invention it is important to be able to correlate the biopsy specimens with their corresponding markers so that the subsequent pathological analysis of the biopsy specimens can then be translated to the specific location of the specimens in the target tissue. This enables one to visually define specific pathological images of the target tissue based on the location of the markers on an anatomic image thereof or, if detectable thereby, a functional or hybrid image of the two. The marker images can be correlated with their respective biopsy specimens by any suitable means as would be apparent to those of ordinary skill in the art in view of the instant disclosure.

In its simplest form, the specimens can be correlated to marker location by manually recording the marker type and marker location at the time of excision. As will be apparent to those of ordinary skill in the art, more sophisticated techniques involving coordinate grids, computer software and tracking modalities may also be employed. To illustrate, the patient's first biopsy procedure is frequently completed with the patient in lateral decubitus position in the urologist's office utilizing a TRUS probe that allows the biopsy sample to be taken through the end of the TRUS imaging probe. Biopsy tissue is extracted from each biopsy needle and placed into individual sample transport cassettes, tubes or similar appropriate packaging to protect and preserve the tissue sample. The outer packaging of the tissue transport system (cassette, tube, etc.) may be marked with directions and/or pathology prescription for sample processing. For example, the pathology prescription may request that the sample be recorded as to glandular location such that the histopathology report will track and report tissue sample findings with respect to biopsy tissue locations (e.g., base/apex, right/left side, lateral/medial). In accordance with the invention, biopsy samples may further be described with respect to unique identifiers associated with tissue to marker location. This may be accomplished by tracking unique markers with, for example, numeric, alphabetic or alpha-numeric systems which are recorded manually or otherwise in the patient file, image set, CD, DVD or video recording and on each sample transport package for histopathology sample tracking.

Alternatively, software systems may be employed in conjunction with TRUS and treatment planning systems, such that the marker record with pathology sample identifiers are loaded into a computerized tracking or software device either during the procedure or translated to the computerized patient record from notes made at the patient table post-procedure. Still further, surgical kits may be provided which include unique marker identifiers, such as pre-printed bar code stickers, so that each tissue sample may be identified with its correlation to each marker, in addition to the biopsy site gross anatomic determinants (e.g., apex base, right/left, medial/lateral). In this embodiment, such software will preferably be able to load detailed location information into the computer and be input or printed at the time the individual biopsy tissue samples are labeled. In yet another embodiment, surgical kits can be provided to include tissue sample dyes which may relate to specific tissue sample markers (e.g., blue dye for left lateral apex and red dye for right medial base, etc.).

In still further embodiments, more elaborate biopsy planning and correlation procedures can include a stepper carriage with an attached acrylic rectangular template mounted to a stand or operating room table for stabilization during the image assisted procedure. A biplanar ultarsound probe, MR or MR rectal array probe, or CT guided system may be connected to the template/stepper carriage. A series of, for example, transverse ultrasound views 5 mm apart from the base to the apex of the prostate may be obtained. The location of the urethra and rectum at each of these levels may be recorded and stored. Prior to biopsy needle placement, the probe may be placed at the reference plane and the contours of the prostate gland and anterior rectal wall outlined. The course of the urethra can be shown in overlay. The needle location may be tracked utilizing a biopsy needle with echogenic tip visible on the ultrasound. The actual location of each needle in the reference plane may be measured and marker positions recorded with reference to location relative to urethra, base and apex of prostate and anterior rectal wall. These images define the depths of the "base plane," "apex plane," and "reference plane." The location of the base plane determines the depth of needle insertion. As each needle is placed, its template coordinates (i.e., column and row) may be entered into the planning system and its actual location in the reference plane digitized with a pointing device. Together with the previously determined location of the template, planning systems may calculate the needle trajectories.

Images may be displayed on the live ultrasound image, for example, at each contour level, and this record may be saved on the computerized treatment planning programs. Spot fluoroscope images may be acquired to record marker placement for post-implant record correlation. Newer computer-aided 3-D treatment planning systems may also assist. Post implant CT images may be used, in particular 3-D-based CT planning programs may correlate marker placement. A surgical kit may be provided such that at the time of biopsy tissue excision spot images (e.g., Fluoroscopy) and/or alternative image tracking for marker placement may be designated according to its coordinating biopsy sample. In this manner, bar codes, computer generated location identifiers or, alternatively, US, MR, CT, X-Ray or other image coordinate designations may be used to construct identifier codes for each biopsy sample. Thus, biopsy histopathology results can be reported to correlate with patient implanted markers which designate by unique marker characteristics the histopathology results for future correlation to unique implanted marker sites which may be used to guide follow-up biopsy and image guided treatments.

Once the biopsy is complete and the marker or markers in place, one will ideally have obtained at least one anatomic image of the target tissue which provides an initial data set showing the anatomic volume of the target tissue and a more precisely defined set of target areas within the target tissue defined by the marker images. Depending upon the pathological analysis of the biopsy specimens, these target areas can function as specific biologic target areas for the subsequent application of therapy, or to define a biologic target volume within which therapy can be subsequently directed to the target tissue with, if indicated, variable intensity.

In accordance with the method of the invention, such baseline anatomic images are used in combination with additional imagery to provide an ideal data set for defining biological target areas or volumes of occult tumor foci within the target organ or tissue. More specifically, the anatomic images can be co-registered or fused to one or more functional images to compare the functional image-defined tumor area against the specific marker location, such that the target zone may be expanded to include a larger region and/or the positive area identified by biopsy marker can be used to define a focal area for treatment. Alternatively, in the case of a patient with unconfirmed disease (negative biopsy result), but otherwise presenting with strong clinical suspicion for disease (e.g., rising PSA, positive DRE), those sites identified with markers correlating to negative biopsy sites may be utilized with future functional and anatomic images to direct future biopsy at alternative sites.

More specifically, with the markers in place, one can then obtain any number of subsequent anatomic images, functional images or combinations or hybrids thereof and correlate the information and data provided by those images with the pathology of the target tissue at the marker locations. Advantageously, this is possible whether the subsequent image or pathological data is obtained at the same time or place. Thus, physicians can continue to build an ever more refined picture of the pathology of the target tissue using the definitive pathology defined by the marked biopsy locations as a frame of reference. For example, where an abnormality on a functional image is confirmed to be cancerous based on its correlation with a target area or volume defined by the pathologically confirmed markers, the functional image can then be used to reduce the focal target area, decrease dose intensity or direct therapy to other regions in the target tissue which have not been pathologically confirmed but which show a corresponding abnormality in the functional image suggesting presence of occult tumor foci or volumes. Correlation of the pathology of the marker sites with abnormalities in the functional image can also be used to confirm the accuracy and veracity of the functional image study itself.

To illustrate, a functional image study can be fused to a pelvis image using CAT or MRI and the markers used to help define a biological target volume for dose intensification. As noted above, current functional studies such as ProstaScint® SPECT, FDG or C-11 Choline Positron Emission Tomography (PET), and Magnetic Resonance Spectroscopy Imaging (MRSI) often lack adequate sensitivity and specificity to provide confident information to the clinician providing treatment. By marking and tracking the original biopsy locations through anatomic image modalities, the defined sites can be correlated to the volumes showing abnormal signals in the functional image. If the functional study is reported to have high correlations (e.g., tracer uptake pattern, spectroscopy findings) consistent with marker location and histopathology results, the confidence in the functional study to have detected yet occult regions of tumor would be enhanced and may further justify the use of functional studies in treatment planning of, for example, IMRT, brachytherapy, cryotherapy, other local treatment modalities; and or may serve as a surrogate marker for response to therapy in clinical trials.

Suitable image modalities for capturing the marker images will be apparent to those of ordinary skill in the art in view of this disclosure. For example, one can obtain image data sets using any of CT, MR, X-ray, US, Fluoroscopy or a combination or hybrid thereof. Any of the foregoing technologies which are suitable for detecting the markers and creating an anatomic image will provide a useful data set comprising marker location within the target tissue and the corresponding pathology of the tissue at each marker. In accordance with the invention, it is desired to build on the data set by obtaining functional image data sets (e.g., SPECT, PET, MRSI or a combination or hybrid thereof) and correlating the functional image to the target areas or volumes defined by the marker images. In this way, one can correlate regions of the functional image with the definitive pathology associated with the marker locations and use this data to prescribe and thereafter apply therapy. Thus, it is possible to even further refine diagnosis and treatment using a data set comprised of both anatomic and functional images, or hybrids thereof using commercially available image fusion software, such as Hawkeye Infinia SPECT/CT, Volumetrix Software and Discovery PET/CT from GE Healthcare; Hermes Workstation from Hermes Medical Solutions; AVIA Fusion 7D from Hitachi America Medical Systems; MedView VolumeReg from Medimage; MIM from MIM Vista; Syngo Image Fusion and eSoft Image Fusion from Siemens Medical Solutions; Syntegra GEMNI/Pinnacle3 from Philips Medical Systems; MRSI PROSE Prostate Package software from General Electric Medical Systems; and, IMRT BAT BMode Acquisition and Targeting. Of course, images may be inherently registered when hybrid images are acquired on the same system.

Thus, patients identified as having cancer on positive histopathological findings are most frequently referred for selection of definitive therapy options. Those patients who select, for example, radiation therapy are referred to radiation oncologists for treatment, and those who elect other local therapies are referred to other appropriate oncologists. Alternatively, the diagnosing urologists may treat the patient or the patient may receive treatment from another urologist for such treatment modalities as complete gland excision, high intensity focused ultrasound (HIFU), or cryotherapy. Prior to therapy, patients typically receive anatomic imaging, such as CT, MR or US and, in accordance with the preferred embodiments of the invention, functional imaging such as SPECT, SPECT/CT, PET, PET/CT, SPECT/MRI, MRSI or combinations or hybrids thereof, to stage disease and for treatment planning in accordance with the invention. Once the histopathological and image data are gathered and correlated to provide a useful data set which collectively provide a picture of the pathology of the target tissue, it can then be used to define biological target areas or volumes for purposes of prescribing treatment. Based on the pathology associated with respective markers, as augmented by the functional imaging, one can plan the therapy of the target organ or tissue so as to modulate dose to maximize its effectiveness and minimize harmful side effects or tissue damage. As noted above, to facilitate this analysis it will sometimes be advantageous for the markers themselves to be visually distinguishable from each other on the images or other data sets.

As will be apparent to those of ordinary skill in the art in view of the present disclosure, the process of prescribing therapy comprises the use of the visual data derived from the correlation of the markers and pathology to plan the subsequent treatment. Typically, the gross target volume (GTV) is defined by the anatomic studies with a clinical target volume (CTV) typically comprising the GTV plus an adequate margin to account for microscopic disease at the edge of the GTV and to allow for day-today motion of the GTV from the position at the time of planning, as well as to account for daily error in set up of the patient. Ultrasound or x-ray, for example, are used to see the image visible markers to allow tighter CTV to the GTV by eliminating target motion day to-day and reducing margins to on the order of 4-8 mm. A biological target volume (BTV) typically represents a region defined by a functional study that may be completely within the GTV, or may expand the GTV by showing disease extending beyond the margins defined by the GTV on the anatomic study.

As will be apparent to those of ordinary skill in the art, the visualized markers of the invention will assist in defining and refining such biological target areas for purposes of treatment planning and application of therapy. BTV targeting may be achieved manually, by viewing a biopsy marker found to correlate with positive histopathology on one image set and manually applying that information to the treatment planning system (e.g., left lateral apex), such that the treatment dose would be increased to the BTV, or with the aid of treatment planning systems, such as computerized treatment planning software.

An example of computerized treatment planning software utilization in prostate cancer procedures is described in Stone, N. N., et al., Brachytherapy 2(1), March 2003, pp. 17-25, for the registration of radioactive seeds. This procedure can be readily adapted to the instant method making use of the data set generated by the correlation of pathology to marker location Similar to the prostate brachytherapy low dose rate seed implant technique such as that described by Stone et al., which utilizes 5 mm ultrasound slices to reconstruct in three dimensions the dosimetry obtained in the O.R., the location of markers at biopsy positions can be detected by ultrasound, CT scan or MRI and the treatment planning computer can utilize these data sets to assist pre-operatively, intraoperatively or post-operatively in assessment of the therapy plan both prior to and following execution of the plan. These data can then allow utilization of functional BTV volumes to be assessed both before, during and after therapy to assure adequacy of the therapy to treat the individual patient. More specifically, the SPECT/CT, SPECT/MRI and PET/CT, PET/MRI registration process, as well as CT/SPECT/MRSI and CT/PET/MRSI registration, can be made fast and sufficiently accurate to yield a reliable dosimetric analysis using commercially available registration systems, such as MIM from MIM Vista Corp. Since critical normal tissues are often found to reside in dose gradient regions, small shifts in the dose distribution can impact the prediction of complication or complication severity. Standard registration procedures which include the use of the seed or marker distribution as fiducial markers are time consuming and rely on the proper identification of signals due to the same seed on both data sets. In application of such procedures to the instant method, the markers can be identified, for example, on 2 mm slice CT data set using automatic identification procedures on a reconstructed three-dimensional data set. Marker positions on 3 mm slice thickness T2 MR data sets can be identified using a point-and-click method on each image. Marker images identified on more than one MR slice can be used to determine average marker coordinates for MR images and matched marker pairs between CT and MR images. A least-squares method may be applied to the CT and MR marker coordinates to produce optimum registration. Various commercially available treatment planning systems which can be employed in application of the present method include VariSeed and Eclipse EXT from Varian Medical Systems; KonRad Inverse TPS from Siemens Medical; RAHD 3D/Pro from RAHD Oncology Products; Xplan from Radionics; OptiRad 3D from Permedics; CORVUS from Nomos; PrecisePLAN from Eleckta; ERGO TPS from 3D Line Medical Systems; BrainScan TPS from BrainLab and RTSuite from Multidata Systems.

Advantageously, because the data set used to produce the treatment plan can distinguish and differentiate the specific pathology and tumor progression or aggressiveness of different regions of the target tissue, the treatment plan can be used to direct therapy to different regions of discrete BTV tissue at different intensities.

With the treatment plan in place, one can then proceed to apply therapy to the target BTV in accordance therewith. As will be apparent to those of ordinary skill in the art in view of the instant disclosure, the inventive method is useful to define a biological target area or volume for the direction and application of any suitable therapy, including IMRT, EBRT, Cryotherapy, LDR, HDR, Hyperthermia, Photo Dynamic Therapy (PDT), Gene Therapy, High Intensity Focused Ultrasound (HIFU) and the like.

COMPARATIVE EXAMPLE

In this example, it was attempted to correlate biopsies to a functional image study obtained after the biopsy procedures were completed. The patient in this example underwent a series of biopsies by his local urologist which were non-diagnostic. The patient then underwent a saturation biopsy technique at the Cleveland Clinic where numerous biopsies were obtained from throughout the prostate volume, for which five of eight biopsies from the right lobe were confirmed by pathology to contain adenocarcinoma. These samples were tracked either by manual markings on each tissue sample container, or alternatively using red or blue dye, to allow pathology records to report histopathology findings designating report correlation to grossly identify the sample having originated in either the general left or right prostate. Following the biopsies a SPECT ProstaScint® (Cytogen Corp.) and CT scan were obtained and co-registered or fused. The image fusion was accomplished using commercial software (MIMvista Corp.). The urologist who made the diagnosis for the patient reviewed the image and believed that it may likely correlate to the regions he had biopsied on the right, which were positive, but unlike the method according to the invention, no markers were placed at the time of any of the prior biopsies. Treatment was delivered to the patient using a combination of 3-D conformal external beam radiation for 25 treatments over five weeks, followed by LDR brachytherapy with additional sources placed in the volume defined by the SPECT/CT ProstaScint® functional image uptake. Had markers been placed at the time of the diagnostic biopsy in accordance with the present invention, this informational data set would have been readily available to more accurately define the target volume for treatment.

Modifications and variations of the invention will be apparent to those skilled in the art in the light of the foregoing detailed disclosure. Therefore, it is to be understood that, with the scope of the appended claims, the invention can be practiced otherwise than as specifically shown and described.

The invention claimed is:

1. A method of correlating a functional image of a target tissue to a pathology of said target tissue comprising:
   a) obtaining at least one biopsy specimen from said target tissue at a corresponding biopsy location;
   b) placing a detectable marker in contact with said target tissue substantially at said biopsy location, and correlating said marker to said biopsy location;
   c) obtaining a pathological analysis of said biopsy specimen and correlating said pathological analysis of said specimen to said biopsy location;
   d) obtaining at least one anatomic image of said target tissue which detects a location of at least one said detectable marker;
   e) obtaining at least one functional image of said target tissue; and,
   f) correlating the location of said at least one detectable marker with a corresponding location on said functional image,
   whereby said pathological analysis of said target tissue corresponding to said location of said at least one detectable marker can be correlated to a diagnosis of said target tissue produced by said functional image at said location of said at least one detectable marker.

2. The method of claim 1 wherein said anatomic image is selected from CT, MR, Xray, US, Fluoroscopy or a combination or hybrid thereof.

3. The method of claim 1 wherein said functional image is selected from SPECT, PET, MRSI, Optical Biopsy or a combination or hybrid thereof.

4. The method of claim 1 wherein said anatomic and functional images are acquired substantially simultaneously.

5. The method of claim 4 wherein said images are acquired as a hybrid or combination image.

6. The method of claim 5 wherein said hybrid or combination image is selected from SPECT/CT, PET/CT, SPECT/MR, PET/MR, SPECT/MR/CT, SPECT/MR/US, SPECT/CT/US, SPECT/CT/MRSI/US, SPECT/X-ray, and PET/X-ray.

7. The method of claim 1 wherein said anatomic and functional images are acquired separately.

8. The method of claim 7 wherein said separately acquired images are co-registered or fused using image fusion software.

9. The method of claim 1 wherein said target tissue is a prostate.

10. The method of claim 1 comprising obtaining biopsy specimens and placing said detectable markers substantially at multiple said biopsy locations, and wherein a plurality of said markers are visually distinguishable from each other by at least one said anatomic image, functional image or a combination or hybrid thereof.

11. The method of claim 10 wherein said markers are visually distinguishable based on their size shape, image intensity acoustical impedance, digital marker transmission or wavelength.

12. The method of claim 1 comprising correlating said pathological analysis of said target tissue corresponding to said location of said at least one detectable marker with a diagnosis of said target tissue produced by said functional image at said location of said at least one detectable marker.

13. The method of claim 12, further comprising prescribing therapy to said target tissue based on said correlation, or prescribing one or more additional biopsies to said target tissue at locations other than said location of said detectable marker.

14. The method of claim 13 further comprising applying therapy to said target tissue in at least one region shown by said functional image to be suspicious for cancer.

15. The method of claim 14 wherein said applied therapy is selected from IMRT, EBRT, Cryotherapy, LDR, HDR, Hyperthermia, Photo Dynamic Therapy, HIFU and Gene Therapy.

16. The method of claim 1 further comprising correlating a location of at least one said detectable marker whose corresponding pathological analysis is positive for cancer, with a location of said target tissue shown by at least one said functional image to be suspicious for cancer, and prescribing therapy to said target tissue in at least one other region shown by said functional image to be suspicious for cancer.

17. The method of claim 16 further comprising applying therapy to said target tissue in at least one said other region shown by said functional image to be suspicious for cancer.

18. The method of claim 17 wherein said applied therapy is selected from IMRT, EBRT, Cryotherapy, LDR, HDR, Hyperthermia, Brachytherapy, Photo Dynamic Therapy, HIFU and Gene Therapy.

19. The method of claim 1 comprising:
a) obtaining a plurality of biopsy specimens from said target tissue at a corresponding plurality of biopsy locations;
b) placing a detectable marker in contact with said target tissue substantially at each said biopsy location, and correlating each said marker to each said biopsy location;
c) obtaining a pathological analysis of each said biopsy specimen and correlating said pathological analysis of each said specimen to each said biopsy location;
d) obtaining at least one anatomic image of said target tissue which detects a location of a plurality of said detectable markers;
e) obtaining at least one functional image of said target tissue; and,
f) correlating the locations and corresponding pathological analyses of said plurality of detectable markers with corresponding locations on said at least one functional image;
g) defining one or more biological target volumes based on said marker locations, pathological analyses and a diagnosis produced by said at least one functional image at each said marker location; and,
  i) prescribing therapy to one or more said biological target volumes; or,
  ii) prescribing one or more additional biopsies to said target tissue at locations other than said marker locations.

20. The method of claim 19 further comprising applying therapy to said target tissue within at least a portion of one or more of said biological target volumes.

21. The method of claim 20, comprising applying therapy to at least a portion of at least one said biological target volume at a different intensity than an intensity applied to at least one other portion of said target tissue.

22. The method of claim 20 wherein said step of applying therapy comprises inputting a treatment intensity to be applied to at least one said biological target volume into an electronic treatment planning system.

23. The method of claim 21, wherein said applied therapy is selected from IMRT, EBRT, Cryotherapy, LDR, HDR, Hyperthermia, Photo Dynamic Therapy, HIFU and Gene Therapy.

24. The method of claim 19 wherein said anatomic image is selected from CT, MR, X-ray, US, Fluoroscopy or a combination or hybrid thereof.

25. The method of claim 19 wherein said functional image is selected from SPECT, PET, MRSI, Optical Biopsy or a combination or hybrid thereof.

26. The method of claim 19 wherein said anatomic and functional images are acquired substantially simultaneously.

27. The method of claim 26 wherein said images are acquired as a hybrid or combination image.

28. The method of claim 27 wherein said hybrid or combination image is selected from SPECT/CT, PET/CT, SPECT/MR, PET/MR, SPECT/MR/CT, SPECT/MR/US, SPECT/CT/US, SPECT/CT/MRSI/US, SPECT/X-ray, and PET/X-ray.

29. The method of claim 19 wherein said anatomic and functional images are acquired separately.

30. The method of claim 29 wherein said separately acquired images are co-registered or fused using image fusion software.

31. The method of claim 19 wherein said target tissue is a prostate.

* * * * *